Figure 1:
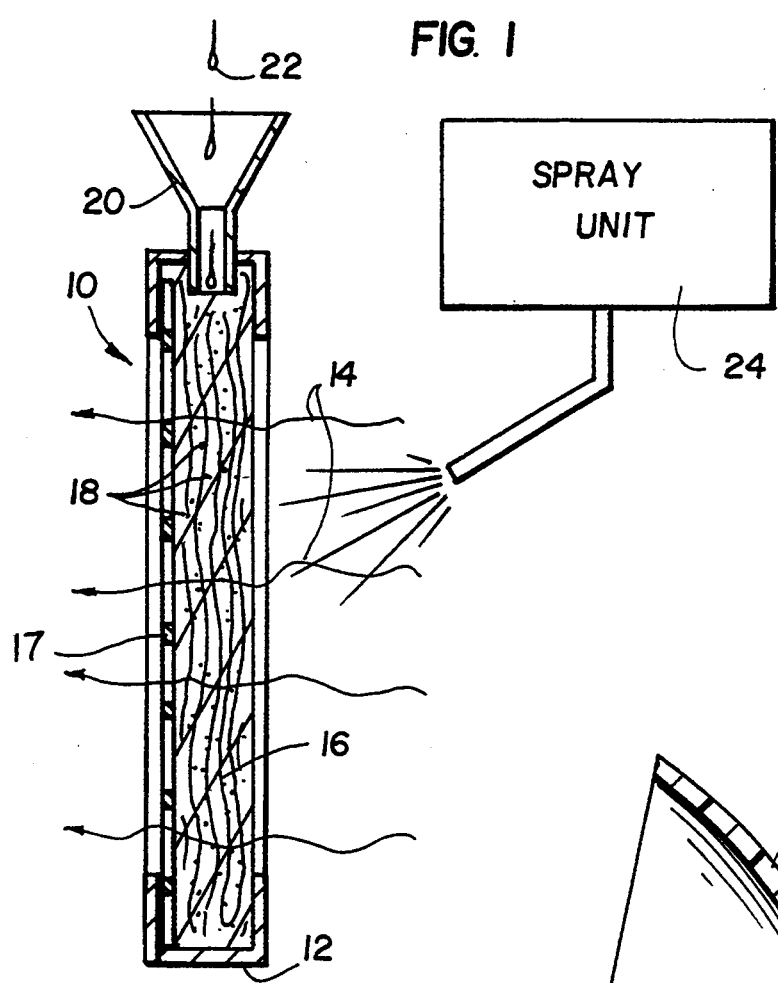

United States Patent [19]

Covarrubias

[11] Patent Number: 5,394,869

[45] Date of Patent: Mar. 7, 1995

[54] METHOD OF INHIBITING BRONCHOSPASMS USING TAURINE IN AN AIR FILTER

[76] Inventor: Jesus Covarrubias, Viale Michelangelo 51, Florence, Italy

[21] Appl. No.: 86,748

[22] Filed: Jul. 6, 1993

Related U.S. Application Data

[63] Continuation of Ser. No. 740,826, Aug. 5, 1991, abandoned, which is a continuation-in-part of Ser. No. 617,153, Nov. 23, 1990, abandoned.

[51] Int. Cl.⁶ .................. A61M 16/00; A61M 15/00; A62B 18/02; A62B 9/00
[52] U.S. Cl. .................. 128/203.29; 128/203.21; 128/203.19; 128/204.11; 128/200.24; 128/200.11; 128/206.12; 128/206.19
[58] Field of Search ............... 128/202.21, 200.24, 128/203.12, 203.15, 203.16, 203.21, 203.29, 204.11, 204.13, 206.19, 203.19, 200.11; 131/331, 335, 337, 355; 502/401; 424/197.1, 498

[56] References Cited

U.S. PATENT DOCUMENTS

| | | | |
|---|---|---|---|
| 3,635,226 | 1/1972 | Horsewell et al. | 131/266 |
| 3,991,773 | 11/1976 | Walker | 131/264 |
| 4,443,354 | 4/1984 | Eian | 128/205.27 |
| 4,498,485 | 2/1986 | Carter | 131/331 |
| 4,649,944 | 3/1987 | Houck, Jr. et al. | 131/336 |
| 4,856,509 | 8/1989 | Lemelson | 128/206.16 |
| 4,865,056 | 9/1989 | Tamaoki et al. | 131/337 |

FOREIGN PATENT DOCUMENTS 0003064 7/1979 European Pat. Off. ............ 131/355

OTHER PUBLICATIONS

Laidlaw et al, "Antimutagenic Effects of Jaurine . . . ", *Cancer Research*, 49, 6600–6604, Dec. 1, 1989.
Milei et al, "Reduction of Reperfusion Injury . . . With Jaurine Bolus", Second World Week of in Updating in Surgery . . . , Un. of Milan, Italy, Jul. 15–21, 1990, VIII/35–VIIP/38.
Gaull, "Taurine as a Conditionally Essential Nutrient in Man", *Jnl. of the American Coll. of Nutrition*, 5:121–125 (1986), © Alan R. Liss, Inc.
Lande, *Alien Property Custodian*, Ser. No. 261,049; Mar. 1939.
Raghu et al, "Probable Mode of Taurine Action", *Indian Jnl. of Experimental Biology*, v20, Jun. 1982/pp. 481–483.
Gordon et al, "Taurine Protects Hamster Brochioles From . . . NO2 . . . ", *AJP*, Dec. 1986, pp. 585–600.
Kimura et al, "Treatment of Smoke-Induced Pulmonary Injury . . . ", *Circulatory Shock*, 25:333–341 (1988). © Alan R. Liss, Inc.
Occupational Heath, "Endotoxins, Cotton Dust, & Cancer", *The Lancet*, Oct. 26, 1985, Enterline et al, pp. 934, 935.

Primary Examiner—Kimberly L. Asher
Attorney, Agent, or Firm—Bryan, Levitin & Bab

[57] ABSTRACT

A method of administering taurine comprises a filtration medium which contains powdered taurine, a breakable capsule which contains a taurine solution or a spraying mechanism. Squeezing or spraying the filtration medium distributes taurine solution in the filter so that it can be picked up by passing air. Powdered taurine may also be provided in the filtration means so that powdered taurine is introduced into the stream of air. Rupturable capsules containing water or other aqueous solution may also be included in the filtration medium with a person in the environment deciding whether to crush the capsules for a humidified administration of taurine solution, or not to break the capsules for the administration of dry taurine into the air.

4 Claims, 5 Drawing Sheets

METHOD OF INHIBITING BRONCHOSPASMS USING TAURINE IN AN AIR FILTER

CROSS REFERENCE TO RELATED APPLICATION

This application is a continuation of application Ser. No. 07/740,826, filed Aug. 5, 1991, now abandoned, which was a CIP of application Ser. No. 07/617,153, filed Nov. 23, 1990, now abandoned.

FIELD AND BACKGROUND OF THE INVENTION

The present invention relates in general to delivery systems for medicinal and nutritional substances, and in particular to a new and useful system for delivering taurine to the lungs of a people in a selected environment, through a specially designed air filter.

An article entitled "Taurine Protects Hampster Bronchioles From Acute $NO_2$-Induced Alterations" by Gordon et al., AJP, December 1986, discloses that Hampsters which were given dietary taurine had improved resistance to the adverse effects of $NO_2$ which is a component of urban pollution and is included in tobacco smoke. One hypothesis disclosed in this article is that taurine is distributed through mammalian tissues and participates in a variety of biochemical reactions to stabilize membranes, scavenge free radicals, and prevent peroxidative injury. The protective effect of taurine on membranes, and against toxic compounds such as oxidants, is also disclosed in "Taurine as a Conditionally Essential Nutrient in Man" by Gaull, J. of Am. College of Nutrition 5:121–125 (1986), which extends these effects to human subjects.

Recently, the intravenous administration of taurine in patients who had undergone coronary artery bypass surgery, was shown to reduce myocardial damage by producing an antioxidant and scavenging effect. See "Reduction of Reperfusion Injury During Myocardial Revascularization with Taurine Bolus" by Ferreira, et al., University of Milan, Jul. 15–20, 1990.

It has also been demonstrated that the administration of nebulized dimethylsulfoxide, by inhalation, is effective in treating smoke-induced pulmonary injury. See "Treatment of Smoke-Induced Pulmonary Injury by Nebulized Dimethylsulfoxide" by Kimura et al., Alan R. Liss, Inc. 1988. These results were based on animal experiments.

Other published test results have established the usefulness of taurine in producing an anti-mutagenic effect by inhibiting various suspected carcinogenic agents that are found to cause changes in DNA. These agents included reactive free radical species. See "Anti-Mutagenic Effects of Taurine a Bacterial Assay System" by Laidlaw et al., Cancer Research 49, 6600–6604, Dec. 1, 1989.

Air filters are conventionally used in a wide variety of selected environments. In residential and commercial buildings, air filters are invariably including in air conditioning and forced air heating systems. Special high efficiency filters are utilized in environments where dust and other contaminants must be excluded, such as the "clean room" of an electronics manufacturing facility and the operating theater of a hospital.

Small portable air filters are also utilized in conjunction with face masks for use by individuals working in a high dust or aerosol environment where contaminants must be kept from entering the lungs of the individual.

SUMMARY OF THE INVENTION

An object of the present invention is to provide a delivery system for taurine in the form of a method for administering taurine through an air filter, and the construction of the air filter itself.

A further object of the present invention is to provide an air filter comprising a filtration medium for filtering air from an environment which passes through the filtration medium and means including taurine in the filtration medium for introducing taurine into the air as it passes through the filtration medium.

A further object of the present invention is to provide a method of administering taurine to the lungs of people in an environment, comprising providing taurine in a filtration medium through which air from the environment passes, for introducing taurine into the air.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

In the drawings:

FIG. 1 shows an air filter using powdered taurine and a source for dripping water;

FIG. 2 shows a mask and filter with powdered taurine and with rupturable capsules of aqueous taurine;

FIG. 3 shows a mask of filtration material in combination with powdered taurine, and with rupturable capsules of taurine solution;

FIG. 4 shows an air filter using powdered taurine and a source for spraying water;

FIG. 5 shows an air filter and a source for spraying taurine;

FIG. 6 shows an air filter and a source for dripping taurine;

FIG. 7 shows a mask and filter with powdered taurine and rupturable capsules of water;

FIG. 8 shows a mask of filtration material in combination with powdered taurine and rupturable capsules of taurine solution;

FIG. 9 shows a mask and filter with powdered taurine;

FIG. 10 shows a mask of filtration material with powdered taurine; and

FIG. 11 shows an air filter using powdered taurine.

DESCRIPTION OF THE PREFERRED EMBODIMENTS

Referring to the drawings in particular, the invention embodied in FIG. 1 comprises an air filter generally designated 10 which includes an outer cardboard or plastic frame 12 which supports a panel of woven or non-woven filtration medium 16, made, for example, of fiberglass, cellulose or similar fibers. A screen or grid 17 supports one surface of medium 16.

In accordance with the present invention, means for introducing taurine into the filtration medium are provided in the form of finely divided powdered taurine 18 which is uniformly distributed through the filtration medium. The powder which should be the consistency of light talcum powder, is automatically drawn into the air 14 as it passes from the filtration medium and to the lungs of a person in the environment serviced by the filter. It is preferable to use 50 to 125 mg of taurine in the filtration medium.

To help add more taurine to the air 14, water 22 may be dripped into the filtration medium 16 through an inlet funnel 20 as shown in FIG. 1. If filter 10 is used in an air conditioning system, a ready supply of water is available from the air conditioning condensers. In the winter, when this water supply is not available, one surface of filter 10 may be sprayed with water from spray means 24. Spray means 24 may be on a timer which sprays enough water to make the filter mediums 16 humid but not enough to saturate the filter medium with water. In the same way the supply of water droplets 22 through funnel inlet 20 may be controlled to avoid overly wetting the filter medium.

Figure 4:
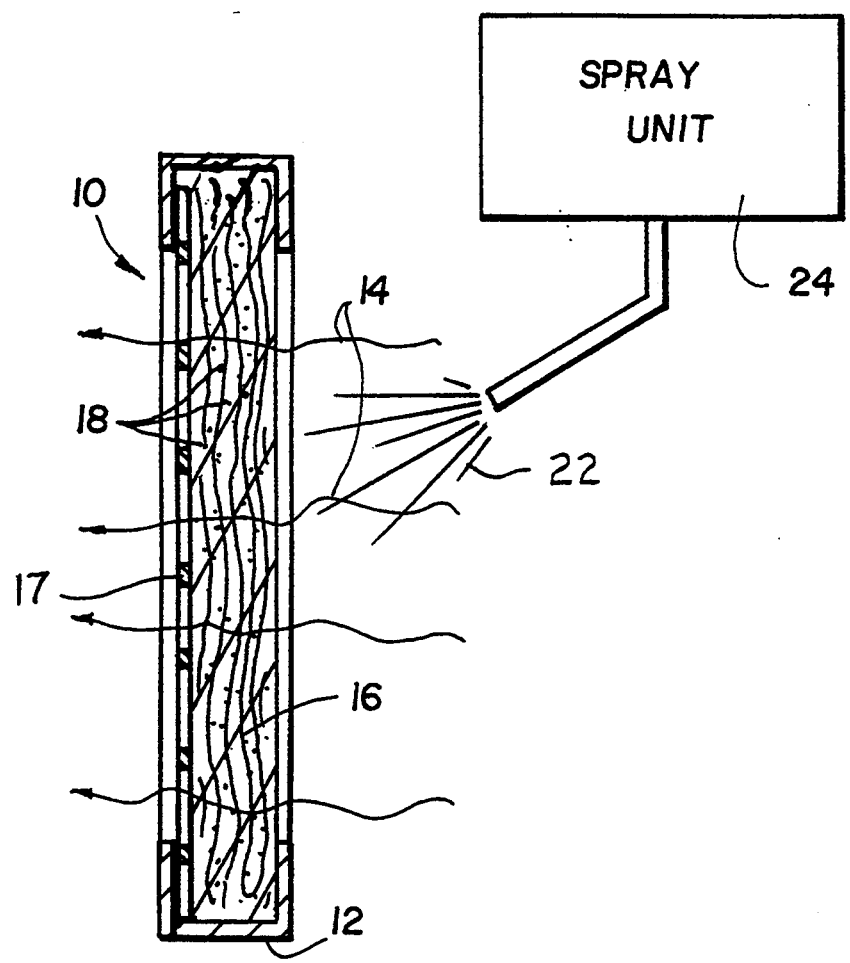
Figure 5:
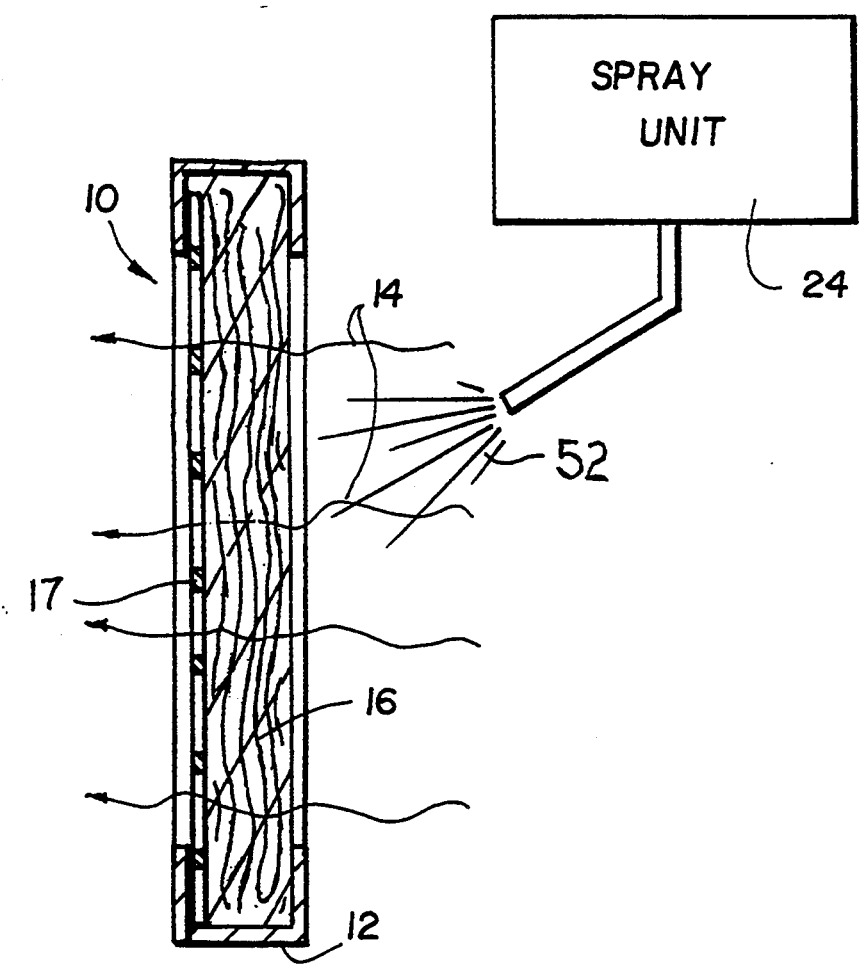
Figure 6:
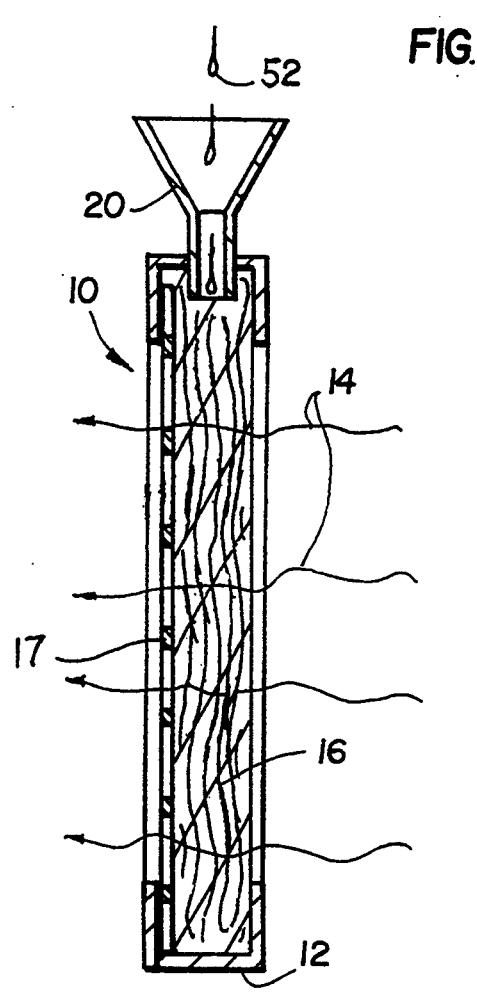

An alternate taurine supply mechanism is to spray a taurine solution through spray means 24, as shown in FIG. 5, or drip the solution at inlet 20 as shown in FIG. 6, at timed intervals onto the filtration medium 16. Water 22 provided to filtration medium 16 through inlet 20 as shown in FIG. 1, or spray means 24, as shown in FIG. 4, can also be at timed intervals. The timed intervals for the taurine solution or water, may be selected to correspond to the time when people in the environment would benefit most from the taurine treatment. For example, a two hour treatment during the morning and another taurine treatment during the afternoon may be advantageous with lunchtime and nighttime periods excluded from the use of water or taurine solution. This conserves taurine during times when people are absent from the environment. Conversely, if filter 10 is used in a home air conditioning system, the taurine supply means can be designed to be active during the evening and night. The use of timed application of taurine to the environmental air may also be useful in optimizing the time when people in the environment are, in effect, treated with taurine to maximize the beneficial effects of the taurine treatment.

Filter 10 may also be utilized in a forced air heating system or in any other commercial, residential, public or private air supply facility.

Figure 7:
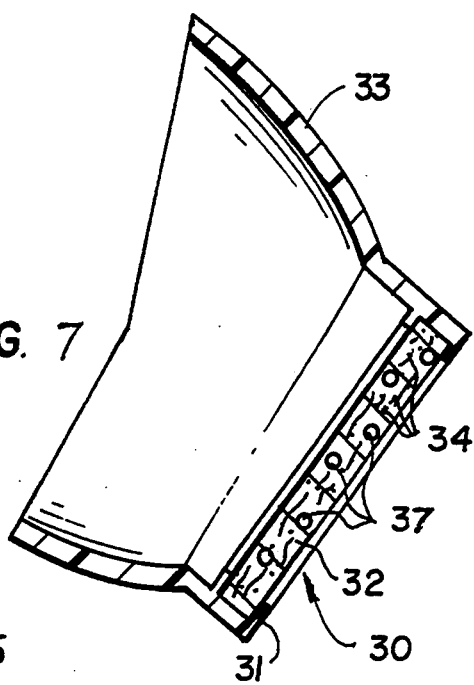
Figure 9:
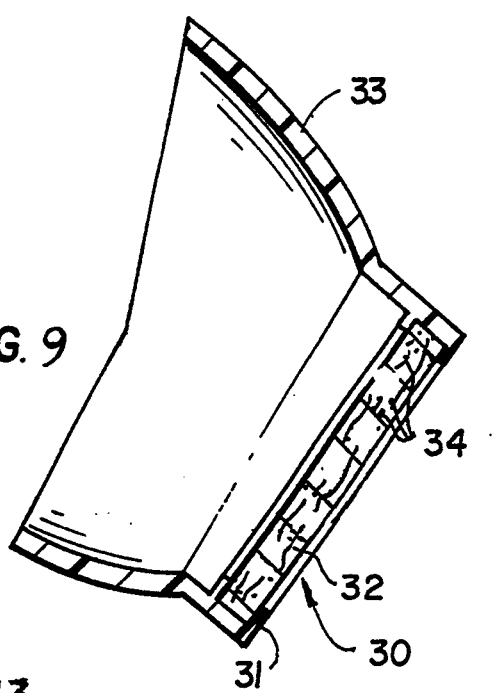

FIG. 9 illustrates a personal air filter mask generally designated 30 having a half-face portion 33 made, for example, of rubber or other resilient material which covers the mouth and nose of a user (not shown). A frame 31 contains an air filter cartridge having filtration medium 32. The filtration medium is impregnated with powdered taurine 34. Alternatively, in addition to the powdered medium, fragile spheres filled with an aqueous solution of taurine 36 (FIG. 2) or water 37 (FIG. 7) are distributed through the filtration medium 32.

If desired, the solution of taurine can be supplied to the filtration medium 36 by pressing the filter between the fingers to crush the delicate water impervious spheres 37 which contain distilled water or a saline or other non-toxic aqueous solution or the taurine solution 36. By crushing the spheres, which for example, may be delicate, thin walled spheres of epoxy resin or other inert substance, the aqueous solution or water is distributed through the filtration medium 32 and forms a solution with the powdered taurine, taurine being soluble in water. The presence of a taurine solution in the filtration medium which is passed by the rapidly moving inhaled air, facilitates some evaporation and some atomization of the solution which is therefore carried into the lungs of the user.

Figure 10:
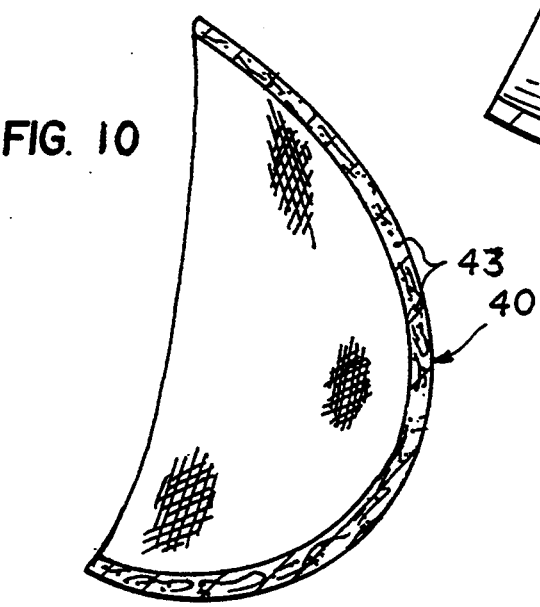

FIG. 10 illustrates a third embodiment of the invention. A paper or other porous half-face mask generally designed 40 is impregnated with taurine powder 43. Due to the masks proximity to the face and the humidity of exhaled air, water from the users lungs will moisten the mask 40 thereby converting the powdered taurine 43 into a taurine solution which impregnates the air being inhaled by the user.

Figure 3:
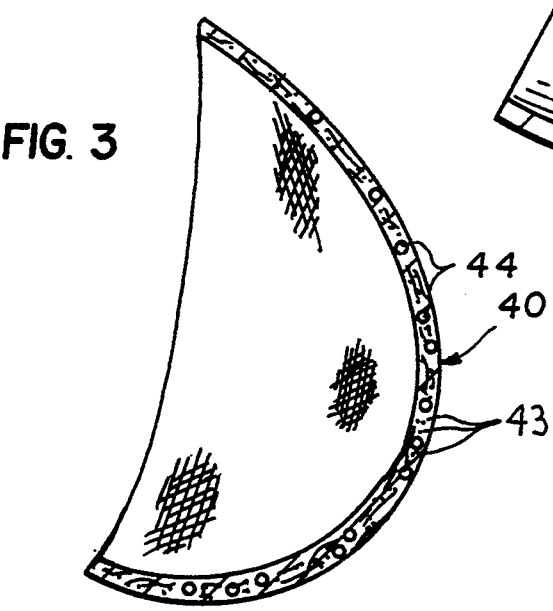

As illustrated in FIG. 3, small spheres 44 containing water, other liquid or taurine solution 45 (FIG. 8) may be included in the material of the mask and may be breakable by flexing or squeezing the mask.

Figure 2:
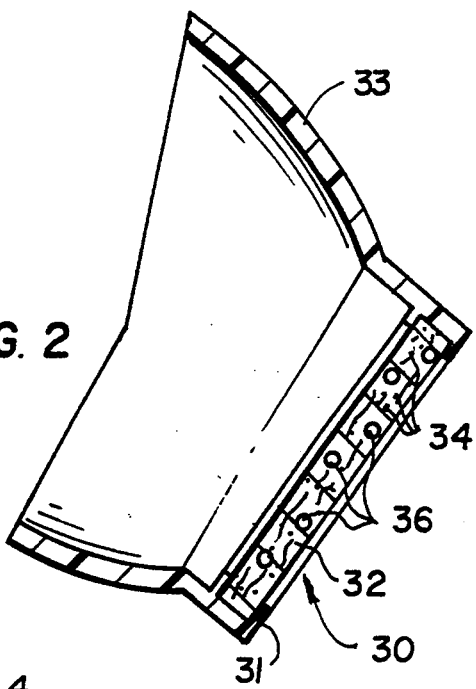

In the embodiments of FIGS. 2 and 3, distilled water or other aqueous solution may be in capsules, with powdered taurine being positioned in the filtration medium 32. The invention also includes a filter such as that shown in FIG. 1, which does not contain the rupturable spheres but which only contains finely. powdered taurine. Alternatively, the capsules contain taurine solution with no powdered taurine in the medium initially for the embodiments illustrated in FIGS 2 and 3.

The presence of even small amounts of taurine in the air demonstrates the effectiveness of the delivery system. As demonstrated in the articles cited as background to this application, even small amounts of taurine, if administered to the lungs, have an advantageous anti-oxidant effect which is particularly synergistic since it will be accompanied by oxidant contaminants in the air such as smoke for example. While activity of the invention is presumed to be in the lungs, the taurine may also act on the contaminants directly to "buffer" them before they reach the person's lungs. This reduces the effect of "second hand" smoke, for example, which has been found to be harmful to non-smokers.

Figure 8:
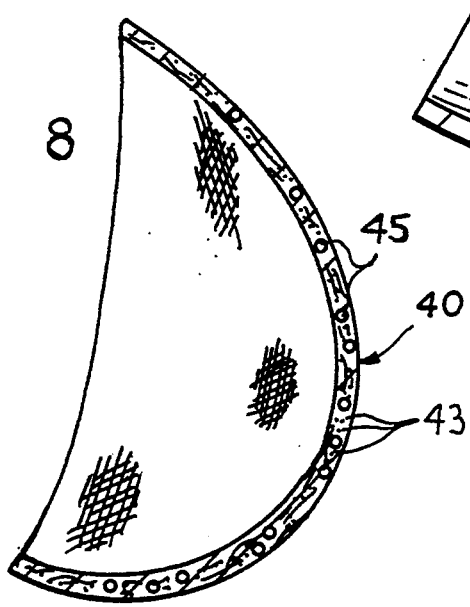
Figure 11:
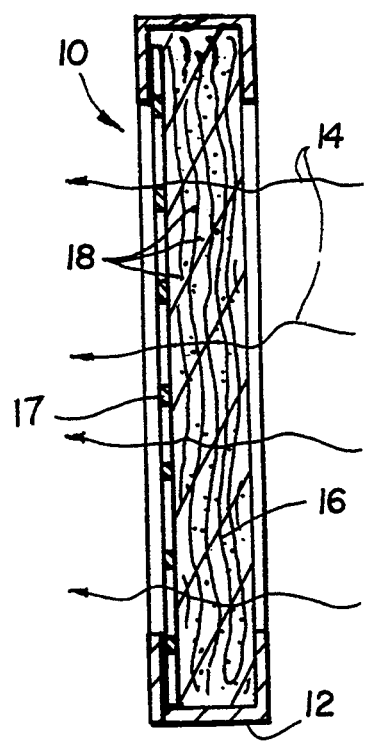

The solution of taurine provided in the capsules in FIGS. 2 and 8 or in the dripped or sprayed solution in FIGS. 5 and 6, should be from 0.2 to 2.0 weight % taurine, in the absence of powdered taurine in the filtration medium. The water containing capsules or spray or dripped water, should be provided so that a solution is formed in the taurine powder containing filtration medium which has approximately 100 mg/ml taurine in water.

A study made by the inventor and by Gianfilippo Bagnato at the Universita' Degli Studi Di Messina Istituto Di Medicina Interna, has established the effectiveness of taurine in relieving smoke-induced injuries in both animals (sheep) and in nine human subjects, ages 10–40. The mode of administration was through inhalation of a taurine solution of distilled water, nebulized by ultrasound. This study established that inhalation of taurine aerosol results in significant inhibition of induced bronchospasm.

In this study, each of the nine patients suffered from bronchial extrinsic and intrinsic asthma. The subjects had any local and general bronchodilator withdrawn for ten days, and then underwent aspecific provocative tests, using distilled water nebulized by ultrasound.

The tests consisted in measuring the main spirometric values by means of a spirometer, both prior and 10 min. after the inhalation of distilled water through an ultrasonic atomizer. The same assessments were repeated after at least 3 days, but following the inhalation of 250 mg of taurine administered 30 min. before the provocative test, in which the nebulized distilled water was inhaled by the patients.

The results of this study are synthesized in Tables 1 and 2. This includes the data concerning the two major parameters, FVC and FEV 1. The data was statistically treated by means of variance analysis. The inhalation of nebulized distilled water resulted in a significant reduction of the parameter FVC (p=0.00002), going from 3.32±0.83 to 2.64±1.06 liters as shown in Table 1.

This behavior underlines that the selected patient presents bronchial instability, which is typical of an asthmatic subject. The same test, performed 3 days later, did not produce significant bronchiospatic variations; in fact the parameter goes from 3.48±0.49 to 3.35±0.33, where "p" is not significant.

Likewise, the comparison between the values prior to the provocative test—3.32±0.83, and 3.47±0.44 liters—was not significant, while the difference between the parameters (measured after the test) is significant.

Analogous considerations can be made from Table 2 which is related to FEV1 values.

In this case too, the difference between the figures assessed prior to and after the inhalation of distilled water (2.42±0.67 and 1.69±0.64 liters, where p is=0.00003) is significant, which shows the $H_2O$-induced reduction of the bronchial caliber, whereas the same aspecific provocative test did not produce significant variations in the bronchial calibre (2.33±0.67 and 2.16±0.21, where "p" is not significant) when this test was carried out after the inhalation of taurine via aerosol.

In this case too, the figures assessed before the inhalation of nebulized distilled water both in the baseline test and in the following one (performed after the inhalation of taurine were not significantly different.

The foregoing data suggests that the inhalation of taurine by aerosol resulted in a significant inhibition of the induced bronchospasm. In fact, both the parameters FVC and FEV1 (selected because of their higher reliability with respect to the values of the flows which were most sensitive, but subject of a greater intrinsic variability) and the other parameters were not reduced following the distilled water inhalation.

The importance of this finding is also stressed by the fact that these parameters were not significantly different before the two provocative tests; in other words this means that the baseline conditions of the subjects taking part in the test were the same. Taurine thus plays a preventive role in the induced bronchospasm.

TABLE 1

| | FVC BEHAVIOR | | |
|---|---|---|---|
| | Before | After $H_2O$ | P |
| Baseline | 3.32 ± .83 | 2.64 ± 1.06 | .00002 |
| After taurine | 3.47 ± .49 | 3.35 ± 0.33 | N.S. |
| P | N.S. | .022 | |

TABLE 2

| | FEV1 BEHAVIOR | | |
|---|---|---|---|
| | Before | After $H_2O$ | P |
| Baseline | 2.42 ± .67 | 1.69 ± 1.64 | .00003 |
| After taurine | 2.33 ± .67 | 2.16 ± 0.21 | N.S. |
| P | N.S. | .041 | |

The inventor estimates that as many as $10^{14}$ free radicals can be neutralized per breath of air from the filter of the present invention. The tests were conducted using 5 ml of water containing 250 mg taurine, in solution. It is estimated that as much as 500 mg of taurine can be dissolved in 5 ml of water.

While specific embodiments of the invention have been shown and described in detail to illustrate the application of the principles of the invention, it will be understood that the invention may be embodied otherwise without departing from such principles.

What is claimed is:

1. A method for inhibiting bronchospasm in a patient, the method comprising the steps of:
   providing an air filter means for filtering air in a selected environment;
   loading said filter means with taurine;
   introducing taurine into air as it passes through said filter means; and
   having a patient inhale the air that has taurine introduced therein.

2. The method according to claim 1, further comprising the steps of:
   providing a face mask;
   providing said air filter means in said face mask; and
   having the patient wear the mask over the nose and mouth of the patient.

3. The method according to claim 1, further comprising the step of:
   loading said filter means with taurine in liquid form.

4. The method according to claim 1, further comprising the step of:
   loading said filter means with taurine in powder form.

* * * * *